(12) United States Patent
Zhao et al.

(10) Patent No.: US 11,067,488 B1
(45) Date of Patent: Jul. 20, 2021

(54) INNER AND OUTER FRAMEWORK COMBINED VARIABLE STIFFNESS ROCK MECHANICS TESTER AND TESTING METHOD

(71) Applicant: SHANDONG UNIVERSITY OF SCIENCE AND TECHNOLOGY, Qingdao (CN)

(72) Inventors: Tongbin Zhao, Qingdao (CN); Yanchun Yin, Qingdao (CN); Yunliang Tan, Qingdao (CN); Minglu Xing, Qingdao (CN); Yue Qiu, Qingdao (CN); Wuwei Zheng, Qingdao (CN); Xinyuan Wang, Qingdao (CN)

( * ) Notice: Subject to any disclaimer, the term of this patent is extended or adjusted under 35 U.S.C. 154(b) by 0 days.

(21) Appl. No.: 17/225,983

(22) Filed: Apr. 8, 2021

Related U.S. Application Data

(63) Continuation of application No. PCT/CN2019/104835, filed on Sep. 9, 2019.

(30) Foreign Application Priority Data

Apr. 12, 2019 (CN) .......................... 201910291663.6

(51) Int. Cl.
*G01N 3/12* (2006.01)
*G01N 33/24* (2006.01)

(52) U.S. Cl.
CPC .............. *G01N 3/12* (2013.01); *G01N 33/24* (2013.01); *G01N 2203/0019* (2013.01); *G01N 2203/0069* (2013.01)

(58) Field of Classification Search
CPC .. G01N 3/12; G01N 33/24; G01N 2203/0019; G01N 2203/0069
See application file for complete search history.

(56) References Cited

U.S. PATENT DOCUMENTS

| 2015/0168282 A1 | 6/2015 | He et al. |
| 2019/0033198 A1 | 1/2019 | Atapour et al. |

FOREIGN PATENT DOCUMENTS

| CN | 206787940 U | 12/2017 |
| CN | 109253932 A | 1/2019 |
| CN | 109269902 A | 1/2019 |
| GB | 2258734 A | 2/1993 |
| KR | 20100117213 A | 11/2010 |

OTHER PUBLICATIONS

International Search Report and Writen Opinion of PCT/CN2019/104835 dated Dec. 30, 2019.
Notification to Grant Patent Right for Invention of CN201910291663.6 dated Mar. 27, 2020.
Office Action of CN201910291663.6 dated Dec. 6, 2019.

*Primary Examiner* — Jonathan M Dunlap
(74) *Attorney, Agent, or Firm* — W&K IP

(57) ABSTRACT

The present disclosure provides an inner and outer framework combined variable stiffness rock mechanics tester and a testing method, relating to the technical field of rock mechanics. The tester includes a stiffness adjusting apparatus, a test loading apparatus, a monitoring system, and a control system. During a test, according to monitoring data, the load of the stiffness adjusting cylinder is controlled through the control system, and the displacement of the inner top beam is adjusted in real time, to ensure that the loading stiffness reaches a design value and remains constant, which solves the technical problem that the loading stiffness of the rock mechanics tester cannot be quantitatively adjusted, and is easy to operate.

6 Claims, 4 Drawing Sheets

INNER AND OUTER FRAMEWORK COMBINED VARIABLE STIFFNESS ROCK MECHANICS TESTER AND TESTING METHOD

CROSS-REFERENCE TO RELATED APPLICATIONS

This application is a continuation of International Application No. PCT/CN2019/104835 with a filing date of Sep. 9, 2019, designating the United states, now pending, and further claims to the benefit of priority from Chinese Application No. 201910291663.6 with a filing date of Apr. 12, 2019. The content of the aforementioned applications, including any intervening amendments thereto, are incorporated herein by reference.

TECHNICAL FIELD

The present disclosure relates to the technical field of rock mechanics, in particular to an inner and outer framework combined variable stiffness rock mechanics tester, a method for adjusting loading stiffness of the tester, and a method for rock mechanics testing using the tester.

BACKGROUND

Rock mechanics testing is a main technical means to obtain formation character parameters in underground engineering such as geotechnical engineering, mining, and tunnel construction. In 1970, Saramon first comprehensively discussed the influence of different stiffness of a tester on deformation characteristics of rock, and proposed to use a tester with higher stiffness to reduce the additional energy acting on the rock, so as to obtain a stress-strain curve after the peak stress. This point of view was later confirmed by researchers and engineers engaged in rock mechanics in rock mechanics testing, so as to obtain a full stress-strain curve of the rock. The method can also be used to analyze a post-peak instability failure process. By analyzing the full stress-strain curve of the rock, mechanical parameters such as deformation modulus, peak strength, residual strength, and impact energy of the rock can be calculated, which provides a basis for the design of rock engineering excavation schemes and stability analysis.

In actual engineering formation, a lithological structure is diverse, and the combination of rock formations often changes. It can be seen that the stiffness of the rock formations is an indeterminate constant. Laboratory tests show that for the same kind of rock, when testers with different stiffness are used for loading, deformation and failure characteristics of the rock show obvious differences, especially the post-peak deformation and failure behaviors. According to the above research, in order to more accurately study real mechanical response characteristics of rock in an underground engineering environment, a rock mechanics tester matching the roof stiffness needs to be selected for rock mechanical property testing of roof with different lithologies. Therefore, it is necessary to provide a rock mechanics tester whose loading stiffness can be quantitatively adjusted and controlled. However, the loading stiffness of an existing rock mechanics tester is generally constant. In order to solve the problem, it is necessary to further improve the existing rock mechanics tester, so that the loading stiffness is adjustable and mechanics-related parameters in line with rock engineering characteristics can be tested.

SUMMARY OF THE INVENTION

In order to solve the technical problem that the loading stiffness cannot be quantitatively adjusted in rock mechanics testing, the present disclosure provides an inner and outer framework combined variable stiffness rock mechanics tester and a testing method. Specific technical solutions are as follows:

An inner and outer framework combined variable stiffness rock mechanics tester includes a stiffness adjusting apparatus, a test loading apparatus, a monitoring system, and a control system, the stiffness adjusting apparatus comprising an outer framework top beam, an outer column, a stiffness adjusting cylinder, and a base, the outer column being fixedly connected between the outer framework top beam and the base, and the stiffness adjusting cylinder being fixed to the outer framework top beam; the test loading apparatus comprising an inner top beam, an inner column, a loading cylinder, a pressure bearing column, and a high-pressure spring, the inner top beam being fixedly connected below the stiffness adjusting cylinder, the inner column being connected between the inner top beam and the base, the loading cylinder being fixed to the base, and the pressure bearing column being fixed below the inner top beam.

Preferably, stiffness of the inner top beam is greater than that of the inner column, an upper end of the inner column passes through the inner top beam, and the high-pressure spring sleeves the upper end of the inner column. Under a load, the inner column of the tester may produce greater tensile deformation. The high-pressure spring is made of a flexible material, and the deformation under an external load is greater than that of a low-stiffness inner column. Superposition of the deformation of the high-pressure spring and the deformation of the low-stiffness inner column further increases an upper limit of elastic deformation and the amount of elastic energy storage of an inner test loading apparatus, thereby further reducing a lower limit of the loading stiffness of the tester.

Preferably, the outer columns are provided with 4, stiffness of the outer column being greater than that of the inner column; the inner column are provided with 4, and a cross section of the upper end of the inner column is T-shaped.

Preferably, the monitoring system comprising a first pressure sensor and a second pressure sensor, the first pressure sensor being disposed between the stiffness adjusting cylinder and the inner top beam, and the second pressure sensor being disposed between the inner top beam and the pressure bearing column.

Preferably, the monitoring system further comprising a displacement sensor, a vertical guide rod, and a horizontal guide rod, the vertical guide rod being fixed to the base; one end of the horizontal guide rod sliding along the vertical guide rod, and the other end being connected to the inner top beam; a short bracket being fixedly disposed on the vertical guide rod below the horizontal guide rod, and the short bracket being provided with the displacement sensor.

Preferably, the control system controls the stiffness adjusting cylinder and the loading cylinder to load, and the control system receives and records monitoring data of the monitoring system in real time.

A method for adjusting loading stiffness of an inner and outer framework combined rock mechanics tester, using the inner and outer framework combined variable stiffness rock mechanics tester described above, includes the following steps:

Step 1: setting a loading stiffness value, and determining a function relationship between a load value of a rock specimen and designed displacement of the inner top beam;

Step 2: transmitting, by the second pressure sensor, the load value of the rock specimen to the control system in real time, transmitting, by the displacement sensor, an actual displacement value of the inner top beam to the control system in real time, and comparing, by the control system, the actual displacement with the designed displacement;

Step 3: when the actual displacement is greater than the designed displacement, controlling, by the control system, the stiffness adjusting cylinder to load to increase the load; when the actual displacement is less than the designed displacement, controlling, by the control system, the stiffness adjusting cylinder to unload to reduce the load; and repeating this step until the actual displacement value is equal to the designed displacement value; and Step 4: repeating, by the control system, the operation of step 3 to ensure that a relationship between the load value of the rock specimen and the actual displacement value during a test satisfies the function relationship between the load value of the rock specimen and the designed displacement of the inner top beam.

An inner and outer framework combined variable stiffness rock mechanics testing method, using the above-mentioned inner and outer framework combined variable stiffness rock mechanics tester, which includes the following steps:

Step A. setting a stiffness value of the tester;

Step B. placing a rock specimen, and transmitting, by the monitoring system, monitoring data of the first pressure sensor, the second pressure sensor, and the displacement sensor to the control system;

Step C. adjusting, by the control system, loading stiffness in real time according to a feedback from the monitoring system, to make a load value of the rock specimen and an actual displacement value of the inner top beam satisfy a function relationship between the load value of the rock specimen and designed displacement of the inner top beam; and Step D. continuously loading the rock specimen through the loading cylinder till instable failure of the rock specimen.

The present disclosure has the following advantageous effects:

(1) The inner and outer framework combined variable stiffness rock mechanics tester provided in the present disclosure realizes loading stiffness adjustment of the rock mechanics tester by the loading of the stiffness adjusting cylinder and the loading cylinder and the deformation of the high-pressure spring and the inner column; and the loading stiffness can be adjusted in real time according to the displacement of the inner top beam and loading stress fed back by the monitoring system, so as to ensure that the stiffness of the tester remains unchanged during the loading.

(2) The first pressure sensor is disposed between the stiffness adjusting cylinder and the inner top beam to monitor and acquire the magnitude of a load applied by the stiffness adjusting cylinder to the inner top beam in real time. The second pressure sensor is disposed between the inner top beam and the pressure bearing column, for monitoring an actual load value of the rock specimen. The displacement sensor is used for monitoring the magnitude of the displacement of the inner top beam in real time.

(3) The method for adjusting loading stiffness of the tester is based on joint action of two cylinders. Firstly, the loading cylinder loads a rock specimen, the rigid inner top beam may move upward under a load, drive the inner column with less stiffness to undergo tensile deformation at the same time, and drive the high-pressure spring to undergo compression deformation at the same time, and elastic energy is stored. Then, the stiffness adjusting cylinder is used to apply a load to limit the displacement of the inner top beam, the tensile deformation of the inner column and the compression deformation of the high-pressure spring. The load applied by the stiffness adjusting cylinder is adjusted by using a monitoring feedback value of the monitoring system, so as to control the displacement of the rigid inner top beam, achieving the purpose of automatic adjustment and control of the loading stiffness of the tester.

(4) The method for rock mechanics testing using the tester can more accurately study real mechanical response characteristics of rock in underground engineering environments.

In addition, the tester also has the advantages of strong reformability, simple operation, and flexible adjustment.

Figure 1:
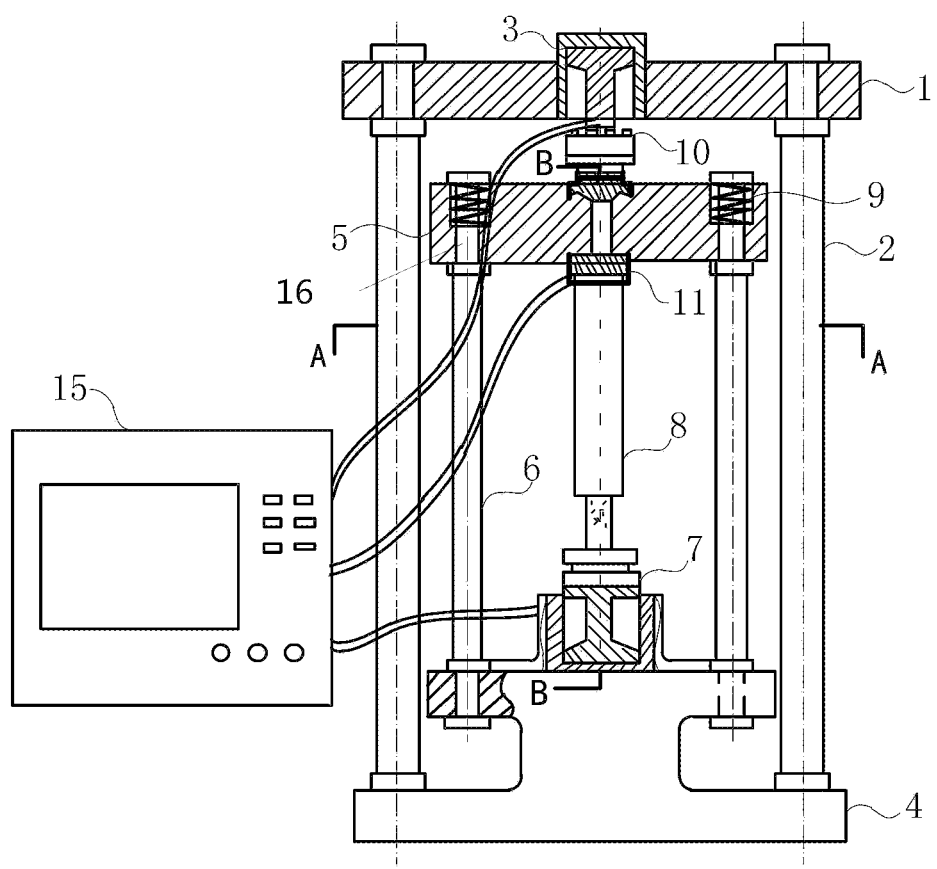
FIG. 1 is a schematic structural diagram of an inner and outer framework combined variable stiffness rock mechanics tester.
Figure 2:
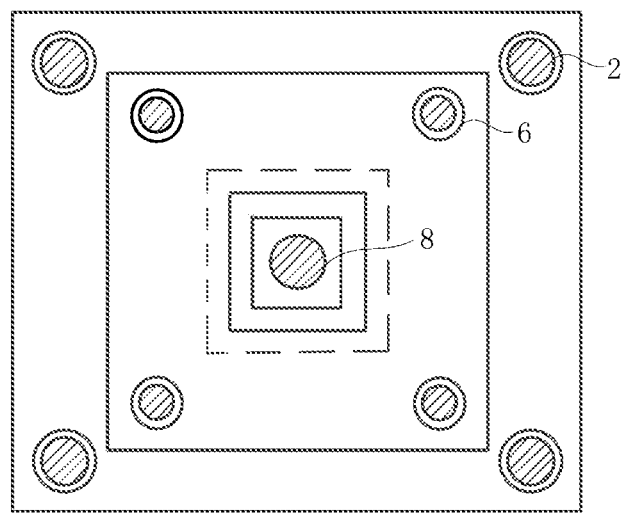
FIG. 2 is a schematic structural diagram of an A-A cross section in FIG. 1.
Figure 3:
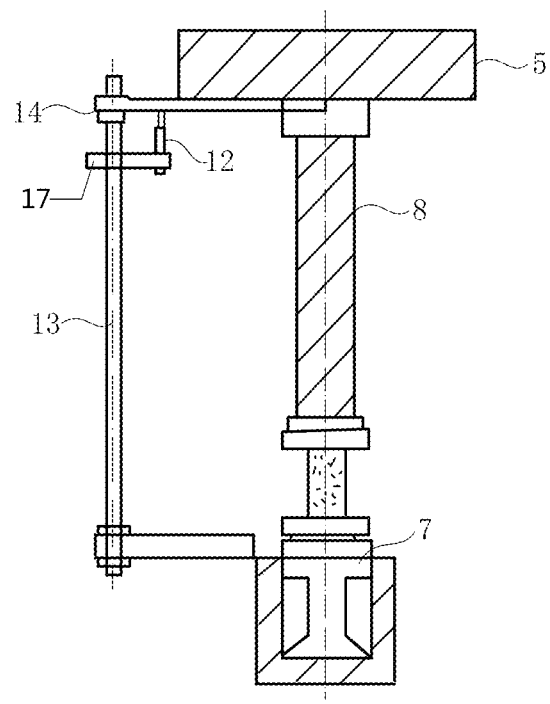
FIG. 3 is a schematic structural diagram of a B-B cross section in FIG. 1.

Reference numerals in the drawings are as follows: 1. outer framework top beam; 2. outer column; 3 stiffness adjusting cylinder; 4. base; 5. inner top beam; 6. inner column; 7. loading cylinder; 8. pressure bearing column; 9. high-pressure spring; 10. first pressure sensor; 11. second pressure sensor; 12. displacement sensor; 13. vertical guide rod; 14. horizontal guide rod; 15. control system; 16. mating hole; 17. short bracket.

DETAILED DESCRIPTION OF PREFERRED EMBODIMENTS

As shown in FIGS. 1 to 5, an inner and outer framework combined variable stiffness rock mechanics tester and a testing method provided in the present disclosure include the following specific implementations.

An inner and outer framework combined variable stiffness rock mechanics tester specifically includes a stiffness adjusting apparatus, a test loading apparatus, a monitoring system, and a control system. The stiffness adjusting apparatus and the test loading apparatus cooperate with each other to adjust the stiffness of the tester. The monitoring system monitors the displacement of an inner top beam and the magnitude of a load applied by a cylinder in real time. The control system controls the operation of the stiffness adjusting cylinder and a loading cylinder to realize automatic adjustment of the loading stiffness of the tester. In addition, the tester also has the advantages of strong reformability, simple operation, and flexible adjustment.

The stiffness adjusting apparatus includes an outer framework top beam 1, an outer column 2, a stiffness adjusting cylinder 3, and a base 4. The outer framework top beam 1 and the outer column 2 are made of high-stiffness materials, and the stiffness of the materials used is greater than 10 N/m, so as to ensure the overall stability of the tester. The outer column 2 is disposed between the outer framework top beam 1 and the base 4. 4 outer columns 2 are provided. Stiffness of the outer column 2 is greater than that of the inner column 6. An overall top view of the outer column 2 of the stiffness adjusting apparatus and the inner column 6 of the test loading apparatus is arranged in a square shape. The stiffness adjusting cylinder is disposed on the outer framework top beam 1. Specifically, the stiffness adjusting cylinder 3 is disposed at a central position of the outer framework top beam 1. The stiffness adjusting cylinder 3 is placed upside down to load downward, thereby limiting the displacement of the inner top beam of the test loading apparatus.

The test loading apparatus specifically includes an inner top beam 5, an inner column 6, a loading cylinder 7, a pressure bearing column 8, and a high-pressure spring 9. The inner top beam 5 is disposed below the stiffness adjusting cylinder 3. The inner column 6 is disposed between the inner top beam 5 and the base 4. The loading cylinder 7 is disposed on the base 4. The loading cylinder 7 loads vertically upward. The pressure bearing column 8 is disposed below the inner top beam 5, for transmitting the loading force and fixing the rock specimen. Stiffness of the inner top beam 5 is greater than that of the inner column. The inner top beam 5 is made of a material with higher stiffness, and the deformation of the inner top beam 5 within the loading range of the stiffness adjusting cylinder 3 is negligible. An upper end of the inner column 6 passes through the inner top beam 5. The high-pressure spring 9 sleeves the upper end of the inner column 6, for adjusting and controlling the displacement of the inner top beam 5. In addition, specifically, 4 inner columns 6 are also provided. The upper end of the inner column 6 and the high-pressure spring are embedded in the inner top beam 5 together and telescopic along a mating hole 16 on the inner top beam 5. A cross section of the upper end of the inner column 6 is T-shaped.

When the tester is in use, if the test loading apparatus is removed, the inner and outer framework combined variable stiffness rock mechanics tester as a whole can be used as a rock mechanics tester with fixed stiffness, and an existing rock mechanics testing machines with fixed stiffness can also be modified.

The monitoring system includes a first pressure sensor 10 and a second pressure sensor 11. The first pressure sensor 10 is disposed between the stiffness adjusting cylinder 3 and the inner top beam 5, for monitoring and acquiring the magnitude of a load applied by the stiffness adjusting cylinder 3 to the inner top beam 5 in real time. The second pressure sensor 11 is disposed between the inner top beam 5 and the pressure bearing column 8, for monitoring an actual load value of the rock specimen. The monitoring system further includes a displacement sensor 12, a vertical guide rod 13, and a horizontal guide rod 14. The vertical guide rod 13 is fixed to the outer framework top beam 1 and the base 4. One end of the horizontal guide rod 14 slides along the vertical guide rod 13, and the other end is connected to the inner top beam 5 and moves with the inner top beam 5. The vertical guide rod 13 below the horizontal guide rod 14 is further fixedly provided with a short bracket 17. The short bracket 17 is provided with the displacement sensor 12. The displacement sensor 12 is used for monitoring the magnitude of the displacement of the inner top beam 5 in real time.

The control system 15 controls the stiffness adjusting cylinder 3 and the loading cylinder 7 to load, the control system 15 receives and records monitoring data of the monitoring system, and the control system adjusts the stiffness adjusting cylinder to load or unload in real time according to a feedback from the monitoring system, so as to ensure that the monitoring data satisfies a function relationship between a load value of the rock specimen and designed displacement of the inner top beam during the test.

Through the research on laboratory tests of rock mechanics, it is found that for the same kind of rock, when testers with different stiffness are used for loading, deformation and failure characteristics of the rock show obvious differences, especially the post-peak deformation and failure behaviors. It can be seen from the above research that in order to more accurately study the real mechanical response characteristics of the rock in the underground engineering environment, the stiffness of the tester needs to be adjusted during the test to avoid a test error caused by the different loading stiffness.

Figure 4:
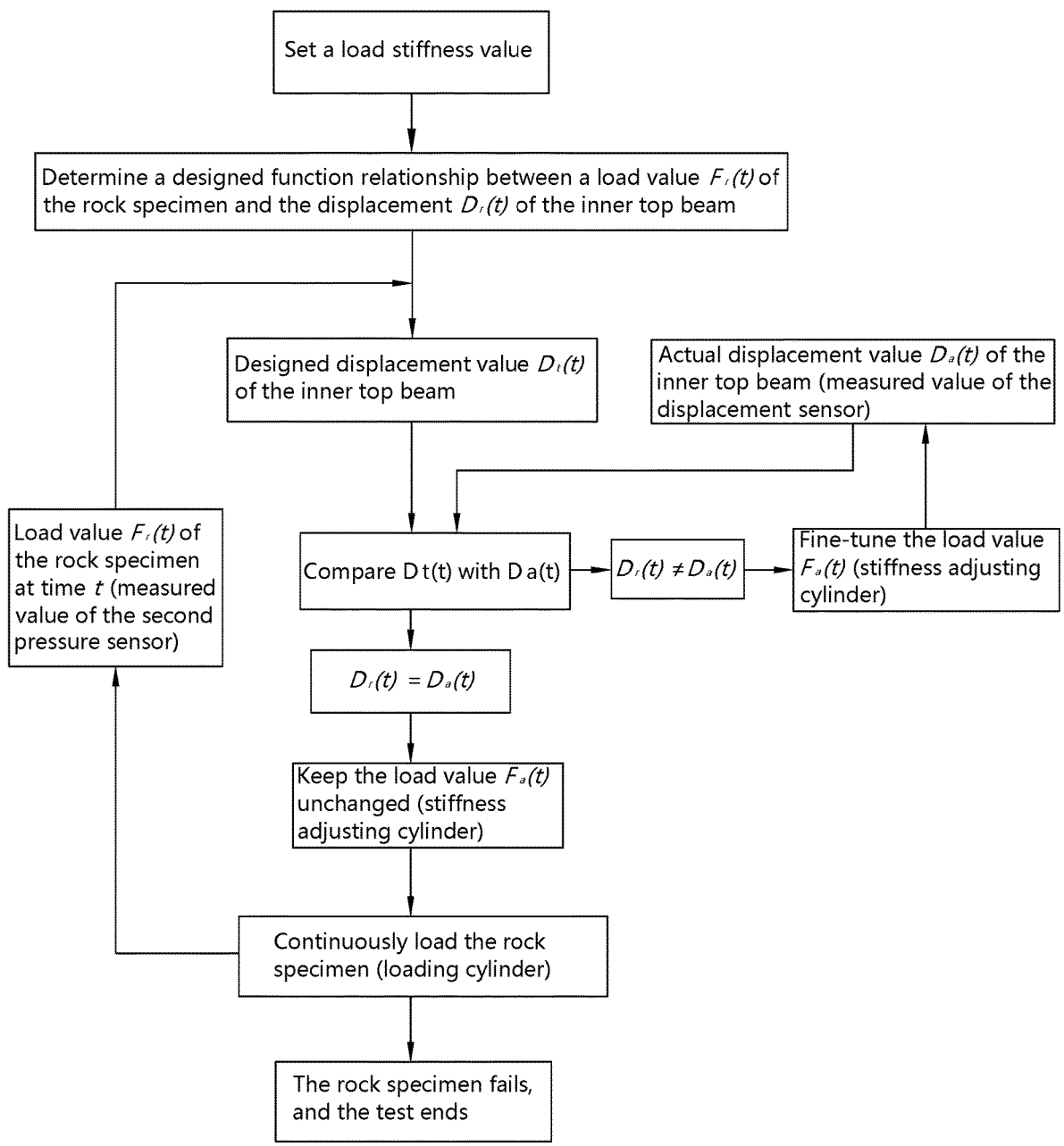
FIG. 4 is a flowchart of a method for adjusting loading stiffness.
Figure 5:
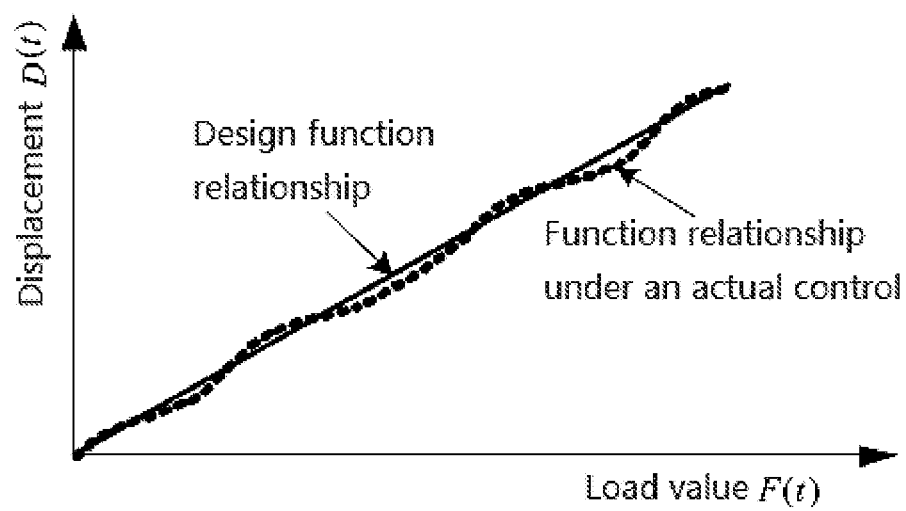
FIG. 5 is a diagram of a function relationship between a load value of a rock specimen and displacement of an inner top beam.

The present disclosure provides a method for adjusting loading stiffness of an inner and outer framework combined rock mechanics tester, using the inner and outer framework combined variable stiffness rock mechanics tester described above. As shown in FIG. 4, the adjusting step specifically includes the following steps:

Step 1: A loading stiffness value is set, and a function relationship between a load value of a rock specimen and designed displacement of the inner top beam is determined, as shown by the straight line in FIG. 5.

Step 2: The second pressure sensor transmits the load value of the rock specimen to the control system in real time, the displacement sensor transmits an actual displacement value of the inner top beam to the control system, and the control system compares the actual displacement with the designed displacement.

Step 3: When the actual displacement is greater than the designed displacement, the control system controls the stiffness adjusting cylinder to load to increase the load, so as to reduce the actual displacement; when the actual displacement is less than the designed displacement, the control system controls the stiffness adjusting cylinder to unload to reduce the load, so as to increase the actual displacement; and this step is repeated until the actual displacement value is equal to the designed displacement value.

Step 4: The control system repeats the operation of step 3 to ensure that a relationship between the load value of the rock specimen and the actual displacement value during a test satisfies the function relationship between the load value of the rock specimen and the designed displacement of the inner top beam. An actual relation curve during the test is as shown by the curve in FIG. 5.

An adjustment principle of the method is based on joint action of two cylinders. Firstly, the loading cylinder loads a rock specimen, the rigid inner top beam may move upward under a load, drive the inner column with less stiffness to undergo tensile deformation at the same time, and drive the high-pressure spring to undergo compression deformation at the same time, and elastic energy is stored. Then, the stiffness adjusting cylinder is used to apply a load to limit the displacement of the inner top beam, the tensile deformation of the inner column and the compression deformation of the high-pressure spring. When the rock specimen is subjected to the same load value, the greater the load applied by the stiffness adjusting cylinder, the smaller the displacement of the rigid inner top beam, the smaller the energy stored in the inner column with low stiffness, the smaller the impact load when the specimen is destroyed, the greater the loading stiffness of the tester. In the above process, the displacement sensor monitors a displacement value in real time, and the control system adjusts the load applied by the stiffness adjusting cylinder, so as to realize real-time control over the displacement of the inner top beam, which ensures that the loading stiffness reaches a design value and remains constant during test loading and achieves the purpose of automatic adjustment and control of the loading stiffness of the tester.

More specifically, before the test, a loading stiffness value is set according to a specific structure of the tester, to obtain a function relationship between a load value Fr(t) of the rock specimen and a designed displacement value Dr(t) of the inner top beam. During the test, the second pressure sensor of the monitoring system monitors the load value Fr(t) of the rock specimen in real time, the control system determines the designed displacement value Dr(t) of the inner top beam correspond to a certain time, and the displacement sensor measures an actual displacement value Da(t) of the inner top beam at the time. The control system compares the designed displacement value Dr(t) with the actual displacement value Da(t). When the actual displacement value Da(t) of the inner top beam is greater than the designed displacement value Dr(t), the control system controls the stiffness adjusting cylinder to load to increase a load value Fa(t) of the stiffness adjusting cylinder, so as to limit the displacement of the inner top beam, till the actual displacement Da(t) is equal to the allowable displacement value Dr(t). When the actual displacement value Da(t) is less than the designed displacement value Dr(t), the control system controls the stiffness adjusting cylinder to unload to reduce the load value Fa(t) of the stiffness adjusting cylinder, so as to increase the actual displacement value Da(t) to make the actual displacement value Da(t) equal to the allowable displacement value Dr(t). The control system makes the actual displacement value Da(t) of the inner top beam 5 equal to the designed displacement value Dr(t) through constant feedback and adjustment of the displacement information and load information described above, so that the load value Fr(t) of the rock specimen and the actual displacement value Da(t) of the inner top beam satisfy a corresponding function relationship in real time. This ensures that the loading stiffness is a set value and remains constant. During the continuous loading of the loading cylinder, the loading stiffness is maintained constant through adjustment, and the test is ended till failure and instability of the rock specimen.

In addition, the present disclosure further provides an inner and outer framework combined variable stiffness rock mechanics testing method, using the inner and outer framework combined variable stiffness rock mechanics tester and the method for adjusting loading stiffness, specifically including the following steps:

Step A) A specific loading stiffness value of the tester is set according to a test scheme or a loading stiffness value of the tester is set according to a test requirement.

Step B) A rock specimen is placed, the monitoring system transmits monitoring data of the first pressure sensor, the second pressure sensor, and the displacement sensor to the control system, and the control system adjusts the loading of the stiffness adjusting cylinder according to a control principle, so as to adjust the loading stiffness to the set value.

Step C) The control system adjusts the loading stiffness according to a feedback from the monitoring system, to make a load value of the rock specimen and an actual displacement value of the inner top beam satisfy a function relationship between the load value of the rock specimen and designed displacement of the inner top beam.

Step D) The rock specimen is continuously loaded through the loading cylinder till instable failure of the rock specimen.

The method for rock mechanics testing using the tester further reduces an error between a laboratory test and actual engineering by controlling the loading stiffness during the test, and thus can better study real mechanical response characteristics of rock in underground engineering environments.

It should be appreciated that the foregoing is only preferred embodiments of the invention and is not for use in limiting the invention. Although this invention is described in detail based on the foregoing preferred embodiments, it is apparent for those skilled in the art that modification of technical proposals or equivalent substitution of part or all of the technical features can be made. Any modification, equivalent substitution, and improvement without departing from the spirit and principle of this invention should be covered in the protection scope of the invention.

What is claimed is:

1. An inner and outer framework combined variable stiffness rock mechanics tester, comprising a stiffness adjusting apparatus, a test loading apparatus, a monitoring system, and a control system, the stiffness adjusting apparatus comprising an outer framework top beam, an outer column, a stiffness adjusting cylinder, and a base, the outer column being fixedly connected between the outer framework top beam and the base, and the stiffness adjusting cylinder being fixed to the outer framework top beam; the test loading apparatus comprising an inner top beam, an inner column, a loading cylinder, a pressure bearing column, and a high-pressure spring, the inner top beam being fixedly connected below the stiffness adjusting cylinder, the inner column being connected between the inner top beam and the base, the loading cylinder being fixed to the base, and the pressure bearing column being fixed below the inner top beam; the high-pressure spring sleeving an upper end of the inner column, and the upper end of the inner column and the high-pressure spring being embedded in the inner top beam together and telescopic along a mating hole on the inner top beam;

the monitoring system comprising a first pressure sensor and a second pressure sensor, the first pressure sensor being disposed between the stiffness adjusting cylinder and the inner top beam, and the second pressure sensor being disposed between the inner top beam and the pressure bearing column;

the monitoring system further comprising a displacement sensor, a vertical guide rod, and a horizontal guide rod, the vertical guide rod being fixed to the base; one end of the horizontal guide rod sliding along the vertical guide rod, and the other end being connected to the inner top beam; and a short bracket being fixedly disposed on the vertical guide rod below the horizontal guide rod, and the short bracket being provided with the displacement sensor.

2. The inner and outer framework combined variable stiffness rock mechanics tester according to claim 1, wherein stiffness of the inner top beam is greater than that of the inner column.

3. The inner and outer framework combined variable stiffness rock mechanics tester according to claim 2, wherein 4 outer columns are provided, stiffness of the outer column being greater than that of the inner column; 4 inner columns are provided, and a cross section of the upper end of the inner column is T-shaped.

4. The inner and outer framework combined variable stiffness rock mechanics tester according to claim 1, wherein the control system controls the stiffness adjusting cylinder and the loading cylinder to load, and the control system receives and records monitoring data of the monitoring system in real time.

5. A method for adjusting loading stiffness of an inner and outer framework combined rock mechanics tester, using the inner and outer framework combined variable stiffness rock mechanics tester according to claim 1, wherein the method comprises the following steps:
- step 1: setting a loading stiffness value, and determining a function relationship between a load value of a rock specimen and designed displacement of the inner top beam;
- step 2: transmitting, by the second pressure sensor, the load value of the rock specimen to the control system in real time, transmitting, by the displacement sensor, an actual displacement value of the inner top beam to the control system in real time, and comparing, by the control system, the actual displacement with the designed displacement;
- step 3: when the actual displacement is greater than the designed displacement, controlling, by the control system, the stiffness adjusting cylinder to load to increase the load; when the actual displacement is less than the designed displacement, controlling, by the control system, the stiffness adjusting cylinder to unload to reduce the load; and repeating this step until the actual displacement value is equal to the designed displacement value; and
- step 4: repeating, by the control system, the operation of step 3 to ensure that a relationship between the load value of the rock specimen and the actual displacement value during a test satisfies the function relationship between the load value of the rock specimen and the designed displacement of the inner top beam.

6. An inner and outer framework combined variable stiffness rock mechanics testing method, using the inner and outer framework combined variable stiffness rock mechanics tester according to claim 1, wherein the method comprises the following steps:
- step A) setting a stiffness value of the tester;
- step B) placing a rock specimen, and transmitting, by the monitoring system, monitoring data of the first pressure sensor, the second pressure sensor, and the displacement sensor to the control system;
- step C) adjusting, by the control system, loading stiffness in real time according to a feedback from the monitoring system, to make a load value of the rock specimen and an actual displacement value of the inner top beam satisfy a function relationship between the load value of the rock specimen and designed displacement of the inner top beam; and
- step D) continuously loading the rock specimen through the loading cylinder till instable failure of the rock specimen.

\* \* \* \* \*